(12) United States Patent
Campbell

(10) Patent No.: US 8,954,155 B2
(45) Date of Patent: Feb. 10, 2015

(54) APPARATUS AND METHOD FOR REJUVENATING SKIN

(75) Inventor: Mark E. Campbell, Ada, MI (US)

(73) Assignee: Biotalk Technologies Inc, Dallas, TX (US)

( * ) Notice: Subject to any disclaimer, the term of this patent is extended or adjusted under 35 U.S.C. 154(b) by 91 days.

(21) Appl. No.: 13/236,008

(22) Filed: Sep. 19, 2011

(65) Prior Publication Data

US 2013/0073001 A1 Mar. 21, 2013

(51) Int. Cl.
| | |
|---|---|
| *A61N 1/06* | (2006.01) |
| *A61N 1/04* | (2006.01) |
| *A61N 1/20* | (2006.01) |
| *A61N 1/32* | (2006.01) |
| *A61N 7/00* | (2006.01) |
| *A61N 5/06* | (2006.01) |

(52) U.S. Cl.
CPC ............ *A61N 1/0476* (2013.01); *A61N 1/205* (2013.01); *A61N 1/328* (2013.01); *A61N 7/00* (2013.01); *A61N 5/0616* (2013.01); *A61N 2007/0034* (2013.01); *A61N 2007/0047* (2013.01); *A61N 2007/0078* (2013.01); *A61N 2005/0659* (2013.01); *A61N 2005/0662* (2013.01)
USPC .............................................. 607/50; 607/90

(58) Field of Classification Search
USPC ............................................ 607/90, 117, 50
See application file for complete search history.

(56) References Cited

U.S. PATENT DOCUMENTS

| | | | |
|---|---|---|---|
| 2006/0030908 A1 | 2/2006 | Powell et al. | |
| 2007/0032840 A1* | 2/2007 | Peluso | 607/66 |
| 2010/0106075 A1* | 4/2010 | Joshi | 604/20 |
| 2010/0274329 A1* | 10/2010 | Bradley et al. | 607/90 |

OTHER PUBLICATIONS

International Search Report and Written Opinion issued in International Patent Application No. PCT/US2011/052387 mailed on Oct. 24, 2012.
Gavenis, K., et al., "Millicurrent stimulation of human articular chondrocytes cultivated in a collagen type-I gel and of human osteochondral explants", BMC Complementary and Alternative Medicine, 10:43, pp. 1-9 (2010).
Jackson, M.B., et al. "Electrical Development in Spinal Cord Cell Culture", the Journal of Neuroscience, vol. 2, No. 8, pp. 1052-1061 (1982).

\* cited by examiner

*Primary Examiner* — Christopher D Koharski
*Assistant Examiner* — Michael Carey
(74) *Attorney, Agent, or Firm* — Ping Wang; Andrews Kurth LLP

(57) ABSTRACT

A skin rejuvenation device and method for the cosmetic or anti-aging reduction of wrinkles and other skin conditions is disclosed. The skin rejuvenation device comprises an array of positive and negative electrodes for the delivery of electrical microcurrents in the attoampere to milliampere range, light sources to deliver photonic stimulation and/or transducers to deliver ultrasonic stimulation to the skin and underlying tissues.

14 Claims, 12 Drawing Sheets

APPARATUS AND METHOD FOR REJUVENATING SKIN

FIELD

This application generally relates to devices and methods for anti-aging using the device. In particular, the application relates to a system for applying energy stimulation to biological tissue, such as skin, for cellular restoration and reducing wrinkles.

BACKGROUND

Electron transport within mitochondrial membranes leads to the production of adenosine triphosphate (ATP) which is the molecule thought to be the proximate source of energy for various cellular processes. These include the contractile and other processes involved in cellular migrations, the synthesis of various structural and regulatory molecules, the maintenance and turnover of substrate molecules such as collagen and elastin, the processes involved in active absorption of nutrients and active excretion of waste products of cellular metabolism. There resides within and around each cell an extracellular matrix (also known as the ground regulation system or living matrix) composed of various hydrated semiconducting biopolymers that can conduct or semi-conduct electrons and protons from place to place. This matrix connects by a continuous molecular fabric consisting of the integrins and the cytoskeleton that provides continuity with the various organelles within the cells, including the mitochondria. The various skin issues, including age-related changes and pathologies, can compromise the natural flow of electrons and protons to and from the mitochondria.

Aging of the skin shifts the balance between collagen production and breakdown, leading to wrinkles, facial sag and rough skin texture. One dominant theory of aging, known as the free radical theory, suggests that one of the causes of aging is cross-linking of proteins by reactive oxygen species or reactive nitrogen species, frequently referred to as free radicals (Miwa, S et al. (eds.) "Oxidative Stress in Aging: From Model Systems to Human Diseases" (2008) Humana Press, Totowa, N.J.). This cross-linking reduces the flexibility and resiliency of the skin.

With aging demographics, anti-aging dermatological treatments in general and in particular for slowing the effects of aging on the skin of the face, removing blemishes and wrinkles, and revitalizing the skin are becoming increasingly popular. Devices have been marketed that emit various forms of heat, light, sound, electrical currents, magnetic fields and conditioning agents, either individually or in combination, to soften and revitalize skin and reduce or remove wrinkles and to resolve other dermatological issues. Some electrotherapeutic devices use currents above one milliampere (Gavénis K et al. BMC Complementary and Alternative Medicine (2010)10:43). However, currents in biological systems have been measured in the picoampere range. Specifically, patch electrodes placed on the surfaces of cultured neurons have measured picoampere currents in relation to inhibitory postsynaptic potentials (IPSPs), as described by Jackson MB et al. J. Neurosci. (1982) 2(8):1052-1061.

Many skin conditions are also purported to be resolved by chemical treatments such as creams and salves and sprays. Some existing methods for reducing the effects of aging on the skin are based on thermally or chemically injuring the skin to remove the outer layers and thereby stimulate the regenerative processes. Other relatively harsh treatments involve the use of injectable fillers and botulinum toxin, radiofrequency treatments, dermabrasion, laser resurfacing, chemical peeling and microdermabrasion. Ablative laser resurfacing is the most precise technique and is considered by some to be the gold standard for facial skin rejuvenation. While such ablative procedures may be quite efficacious, they carry significant patient downtime and risks of adverse effects. Repeated use of such destructive methods over time can actually damage the skin tissue and thereby create unhealthy conditions such as scarring and dyspigmentation. Therefore, the processes mentioned above can be considered or even harmful in the long term.

SUMMARY

One aspect of the present application relates to a skin rejuvenation device comprising: an applicator comprising at least one positive electrode and at least one negative electrode for the stimulation of skin and underlying tissues with electric currents, an intensity control, and a signal creation source, wherein the device is capable of delivering a current in the attoampere range to the milliampere range.

Another aspect of the application relates to a skin rejuvenation device comprising: an applicator comprising at least one light source for the stimulation of skin and underlying tissues with photonic stimulation, an intensity control, and a signal creation source.

Another aspect of the present application relates to a skin rejuvenation device comprising: an applicator comprising at least one positive electrode and at least one negative electrode for the stimulation of skin and underlying tissues with electric currents and at least one light source for the stimulation of skin and underlying tissues with photonic stimulation, an intensity control, and a signal creation source.

Another aspect of the present invention relates to a method for anti-aging in a subject comprising contacting the skin of the subject to a skin rejuvenation device comprising: an applicator comprising at least one positive electrode and at least one negative electrode for the stimulation of skin and underlying tissues with electric currents, an intensity control, and a signal creation source, wherein the device is capable of delivering a current in the attoampere range to the milliampere range.

Another aspect of the present invention relates to a method for stimulating a skin cell or tissue in a subject comprising contacting said skin cell to a skin rejuvenation device comprising: an applicator comprising at least one positive electrode and at least one negative electrode for the stimulation of skin and underlying tissues with electric currents, an intensity control, and a signal creation source, wherein the device is capable of delivering a current in the attoampere range to the milliampere range.

Another aspect of the present invention relates to a method for anti-aging in a subject comprising contacting the skin of the subject to a skin rejuvenation device comprising: an applicator comprising at least one light source for the stimulation of skin and underlying tissues with photonic stimulation, an intensity control, and a signal creation source.

Another aspect of the present invention relates to a method for stimulating a skin cell or tissue in a subject comprising contacting said skin cell to a skin rejuvenation device comprising: an applicator comprising at least one light source for the stimulation of skin and underlying tissues with photonic stimulation, an intensity control, and a signal creation source.

Another aspect of the present invention relates to a method for anti-aging in a subject comprising contacting the skin of the subject to a skin rejuvenation device comprising: an applicator comprising at least one positive electrode and at least one negative electrode for the stimulation of skin and underlying tissues with electric currents and at least one light source for the stimulation of skin and underlying tissues with photonic stimulation, an intensity control, and a signal creation source.

Another aspect of the present invention relates to a method for stimulating a skin cell or tissue in a subject comprising contacting said skin cell to a skin rejuvenation device comprising: an applicator comprising at least one positive electrode and at least one negative electrode for the stimulation of skin and underlying tissues with electric currents and at least one light source for the stimulation of skin and underlying tissues with photonic stimulation, an intensity control, and a signal creation source.

DETAILED DESCRIPTION

Figure 1:
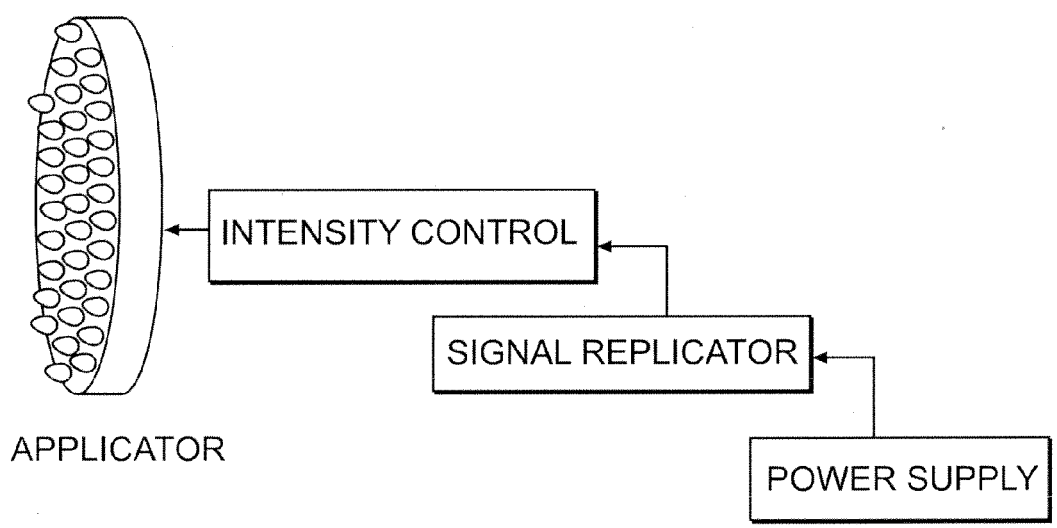
FIG. 1 shows a diagram of the components of the skin rejuvenation device.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

The availability of a number of energetic stimulation devices and skin creams demonstrates the difficulty confronting both the practitioner and the patient, who must learn by trial and error which approach works best for each situation. The consumer, faced with a series of costly professional treatments, would prefer an inexpensive over-the-counter device that the individual can adjust to suit their skin type and the specific condition they wish to treat and that is safe to use at home at suitable intervals to restore and maintain a healthy texture and appearance and functioning of their skin. Ideally, such a system would be conveniently hand-held and either battery operated or connected via an electrical cord to a power source. The present invention meets this need with systems that are safe, painless and effective in removing wrinkles and other skin blemishes. These systems operate by applying electrical and/or photonic energy to the skin via an applicator having an array of conductive electrodes, transducers and/or light sources.

The form and texture of skin is dependent on the activities and arrangements of the skin cells and the manner by which they migrate from place to place and the ways they are joined together. The physical arrangement of the cells depends not only on features of the underlying collagen layer but also on the properties of the various junctional complexes that join cells together and that anchor the cells to the underlying layers of connective tissue, particularly to the dermis and to the superficial fascia. These junctional complexes in turn are composed of a plethora of molecular types. The cell-connective tissue adhesion complexes contain molecules including fibronectin, proteoglycan, laminin, tensin, vitronectin, actin, syndecan, talin, fibroin, vincullin, caveolin and $\alpha$- and $\beta$-integrins, as well as a host of chemical signaling molecules that regulate the metabolism of the junctional components and other aspects of cell metabolism. The cell-cell junctions contain molecules that include claudins, afadin, F-actin, tubulin, myosin, and spectrin/fodrin, as well as a host of chemical signaling molecules that regulate the metabolism of the junctional components and other aspects of cell metabolism. These molecules are mentioned because many of them have an electrical polarity and will therefore be modified by microcurrents introduced into the tissue, and because each molecule will have a resonant frequency that will be influenced by the frequencies of the microcurrents introduced into the tissue. Such microcurrents can cause molecules to migrate or rotate or change shape and thereby undergo an enhancement of their biological effects.

The present application provides an anti-aging method that is easy to perform, painless and very safe. The presently described skin rejuvenation device provides cosmetically significant results after relatively few uses without damaging the skin through heat, chemical exposure or abrasion. Usage of the device has no observable side effects, even with repeated sessions. Successful operation of the device has resulted from experimentation with various designs and configurations including but not limited to variations in electrode or light source number, shape, size and spacing as well as the characteristics of the signal delivered to the electrodes or light sources, including the pattern of activation of electrodes or light sources, frequency, wave shape, duty cycle, and pulse shape. Amplitude modulation of the signal and control of the patterns of activation of the various stimulation means enables multiple effects on various skin conditions with same delivery system.

Energy stimulation using the skin rejuvenation device of the present application leads to a beneficial stimulation of the metabolism of both skin cells and the cells known as fibroblasts, which are responsible for generating and maintaining the collagen network. The active fibroblast produces collagen, which can restore the connective tissue substrate and thereby reverse the aging process. Stimulating collagen synthesis in aged skin reduces wrinkles and improves skin texture. Renewal of the collagen network leads to restoration of the natural weave of the molecular fabric, which in turn proves the natural weave and placement of the cellular components. The benefit of stimulating a person's own collagen production is that collagen deposits in a natural orderly, structured manner and that there is no risk of allergy, immune reaction or infection. With repeated use, the disclosed skin rejuvenation device leads to enhanced vitality of the skin cells, which are then better able to carry out all of the natural functions associated with correcting age-related and other damaging processes that can detract from a vibrant and healthy looking and healthy functioning skin.

The skin is a regenerative tissue in that the cells at the outer surface, the stratum corneum, are continually being lost to the environment and replaced by cells migrating outward from the basal layers, the stratum basale, through the intermediate layers, the stratum spinosum and stratum granulosum. Cumulative damage to skin can occur at various depths, and can be caused by a variety of environmental factors including sunlight (so-called "Photoaging"), exposure to toxic chemicals, burns and the aging processes. These effects can diminish the ability of skin cells to maintain their health and diminish their ability to regenerate and to migrate from place to place. Experience with the device disclosed here has revealed that electrical stimulation can restore the health and vitality of skin cells with consequent aesthetic or cosmetic benefits. These benefits, in turn, can have emotional benefits for an individual whose self-esteem and/or professional life depends upon their appearance.

As used herein, an "operator" is anyone who is using the device on a subject. The operator is inclusive of the subject and any other person and any individual that operates the controls of the device and/or uses the applicator on the skin or other body tissue of the subject.

"Energy stimulation," as used herein, refers to the stimulation of skin or other body tissue with any type of energy including, but not limited to, radiant, electromagnetic radiation (EMR), electromagnetic pulses, electrical currents, infrared, visible light, ultraviolet, magnetic waves, sonic, ultrasonic, and heat.

A "microcurrent device," as used herein, refers to a device that introduces electrical currents into living matter. Electrical current is a measure of the number of charged particles flowing past a particular point in one second. The coulomb is the measure of the number of charges and one ampere represents one coulomb or $6.24 \times 10^{18}$ protons or electrons passing a particular point in one second.

A "milliampere" is one thousandth or $10^{-3}$ of an ampere.

A "microampere" is one thousandth of a milliampere or $10^{-6}$ of an ampere. As used herein, the term "microampere range" means a current of between about 0.1 microampere and about 100 microamperes.

A "nanoampere" is one thousandth of a microampere or $10^{-9}$ of an ampere. As used herein, the term "nanoampere range" means a current of between about 0.1 nanoampere and about 100 nanoamperes.

A "picoampere" is one thousandth of a nanoampere or $10^{-12}$ of an ampere. As used herein, the term "picoampere range" means a current of between about 0.1 picoampere and about 100 picoamperes.

A "femtoampere" is one thousandth of a picoampere or $10^{-15}$ of an ampere. As used herein, the term "femtoampere range" means a current of between about 0.1 femtoampere and about 100 femtoamperes.

An "attoampere" is one thousandth of a femtoampere or $10^{-18}$ of an ampere. As used herein, the term "attoampere range" means a current of between about 0.1 attoampere and about 100 attoamperes.

The term "microcurrent" as used herein is in wide usage in various descriptions in the art. As used generically in this disclosure "microcurrent" may be defined as low level currents in the range of millicurrents down to attocurrents. In the context of this disclosure, the currents employed cover the complete range of currents including millicurrent, microcurrent, nanocurrent, picocurrent, femtocurrent, and attocurrent.

The term "frequency" refers to the measurement of the number of times that a repeated event occurs per unit time. As used herein, "frequency" is measured in hertz (Hz). One Hz means that an event repeats once per second. A further attribute of the technology being disclosed here is the wide range of frequencies of the signals employed, which range from 0 Hz to 999,999 Hz.

In a particular embodiment, the frequency generated or delivered by the device is in the range of about 1 Hz to about 999,000 Hz. In a further embodiment, the frequency generated or delivered by the device is in the range of about 10 Hz to about 900,000 Hz. In a further embodiment, the frequency generated or delivered by the device is in the range of about 100 Hz to about 750,000 Hz. In a further embodiment, the frequency generated or delivered by the device is in the range of about 500 Hz to about 500,000 Hz. In a still further embodiment, the frequency generated or delivered by the device is in the range of about 1,000 Hz to about 350,000 Hz.

In a broad aspect, the application provides a method for causing predetermined physiological changes in a mammalian tissue. The method includes stimulating skin cells and underlying tissues with microcurrents and/or photonic stimulation having power density, frequency, phase and other signal characteristics that mimic or are similar in magnitude to the natural electrical communications known to regulate cellular activities. Safety of the device is assured by the use of low levels of energy stimulation, below the levels that would produce heating of the tissue.

One aspect of the present application relates to a microcurrent device or skin rejuvenation device for stimulating skin cells and underlying tissues with electrical microcurrents for causing predetermined physiological changes in said skin cells and underlying tissues. In a particular embodiment, the skin rejuvenation device provides electrical stimulation as direct current (DC), a unidirectional flow of electric charge from dedicated negative electrodes to dedicated positive electrodes.

In a particular embodiment, the skin rejuvenation device delivers a microcurrent that is of an amperage that is low enough that it does not produce heating of the tissue nor damage the skin cells and underlying tissues. In a particular embodiment, the skin rejuvenation device of the present application is for cosmetic use. In another particular embodiment, the skin rejuvenation device of the present application is for anti-aging use.

One aspect of the present application relates to a device comprising: an applicator comprising at least one positive electrode and at least one negative electrode for the stimulation of skin and underlying tissues with electric currents, an intensity control, and a signal creation source, wherein the device is capable of delivering a current in the attoampere range to the milliampere range.

In a particular embodiment, the electrodes are pin shaped or blade shaped.

In another particular embodiment, the current is in the milliampere range.

In another particular embodiment, the current is in the microampere range.

In another particular embodiment, the current is in the nanoampere range.

In another particular embodiment, the intensity control selectively modulates a signal property selected from the group consisting of amplitude, pulse rate, pulse sweep, frequency, frequency sweep rate, duty cycle and combinations thereof to provide different electrical currents to the skin and underlying tissues. In further embodiment, the frequency generated or delivered by the device is in the range of about 1,000 Hz to about 350,000 Hz.

In another particular embodiment, the device further comprises a power supply for supplying electrical current to the signal creation source. In a further embodiment, the power supply comprises a capacitor. In a further embodiment, the size of the capacitor is between about 1,000 and about 50,000 microfarads.

Another particular embodiment relates to a method for anti-aging in a subject comprising contacting the skin of the subject to the device.

Another particular embodiment relates to a method for stimulating a skin cell or tissue in a subject comprising contacting the skin of the subject to the device.

Another aspect of the application relates to a skin rejuvenation device comprising: an applicator comprising at least one light source for the stimulation of skin and underlying tissues with photonic stimulation, an intensity control, and a signal creation source.

In a particular embodiment, the intensity control selectively modulates a signal property selected from the group consisting of amplitude, pulse rate, pulse sweep, frequency, frequency sweep rate, duty cycle and combinations thereof to provide different photonic stimulation to the skin and underlying tissues.

In another particular embodiment, the device further comprises a power supply for supplying electrical current to the signal creation source. In a further embodiment, the power supply comprises a capacitor. In a further embodiment, the size of the capacitor is between about 1,000 and about 50,000 microfarads.

Another particular embodiment relates to a method for anti-aging in a subject comprising contacting the skin of the subject to the device.

Another particular embodiment relates to a method for stimulating a skin cell or tissue in a subject comprising contacting the skin of the subject to the device.

Another aspect of the present application relates to a skin rejuvenation device comprising: an applicator comprising at least one positive electrode and at least one negative electrode for the stimulation of skin and underlying tissues with electric currents and at least one light source for the stimulation of skin and underlying tissues with photonic stimulation, an intensity control, and a signal creation source.

In a particular embodiment, the intensity control selectively modulates a signal property selected from the group consisting of amplitude, pulse rate, pulse sweep, frequency, frequency sweep rate, duty cycle and combinations thereof to provide different electrical currents and/or photonic stimulation to the skin and underlying tissues.

In another particular embodiment, the device further comprises a power supply for supplying electrical current to the signal creation source. In a further embodiment, the power supply comprises a capacitor. In a further embodiment, the size of the capacitor is between about 1,000 and about 50,000 microfarads.

Another particular embodiment relates to a method for anti-aging in a subject comprising contacting the skin of the subject to the device.

Another particular embodiment relates to a method for stimulating a skin cell or tissue in a subject comprising contacting the skin of the subject to the device.

Skin Rejuvenation Device

Figure 2C:
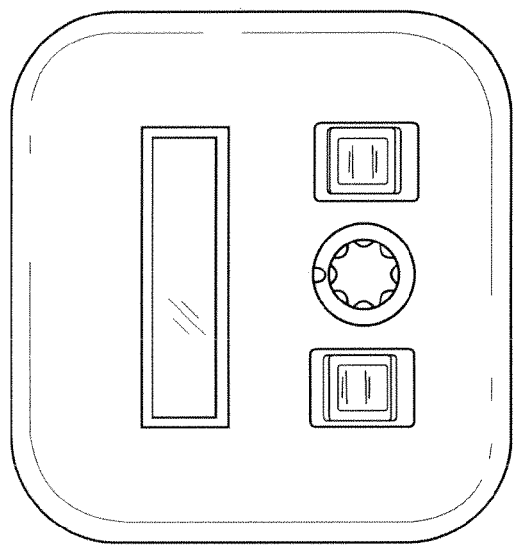
FIGS. 2A-D show different views of an embodiment of the skin rejuvenation device.
Figure 2D:
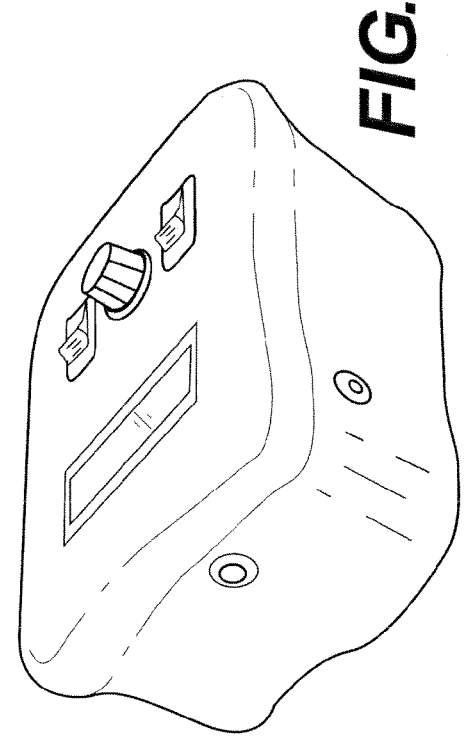
Figure 2A:
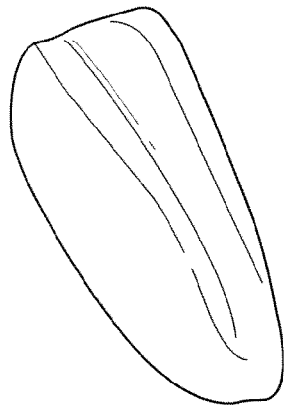
Figure 2B:
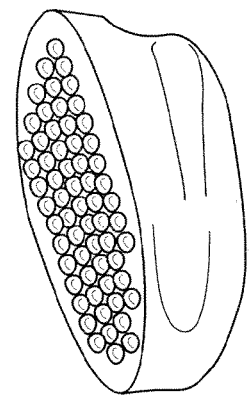

The skin rejuvenation device of the present application comprises four main components as illustrated in FIG. 1: an applicator, a controlling circuit that generates and creates the emission signal of an energy pattern, or "intensity control," a signal generating source (signal replicator, microprocessor) and a power supply. In a particular embodiment, the applicator, intensity control, signal creation generator and power supply are comprised in a single housing. In a further embodiment, the housing is hand-held. In another particular embodiment, the applicator, intensity control, and signal generating source are comprised in a single housing and are connected to the power supply by a cable or multiple cables. In a further embodiment, the housing is hand-held. In another particular embodiment, the applicator and intensity control are comprised in a single housing and are connected to the signal generating source and power supply by a cable or multiple cables. In a further embodiment, the housing is hand-held. In another particular embodiment, the applicator (FIGS. 2A-B) is alone in a housing and is connected to the intensity control, signal generating source and power supply (FIGS. 2C-D) by a cable or multiple cables as exemplified (cable not shown). In a further embodiment, the housing is hand-held. In another embodiment, the intensity control is wireless.

Figure 3:
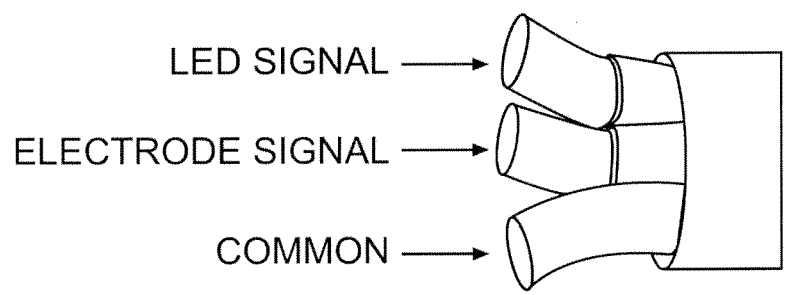
FIG. 3 shows an illustration of a multiple wire cable of the device for carrying independent signals to different elements of the applicator.
Figure 4A:
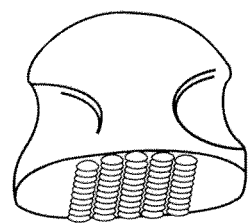
FIGS. 4A-C show an embodiment of the applicator of the skin rejuvenation device.
Figure 4B:
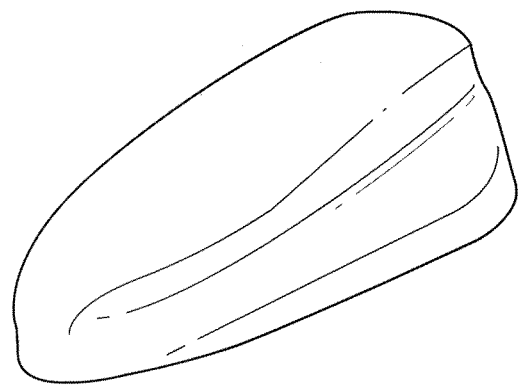
Figure 4C:
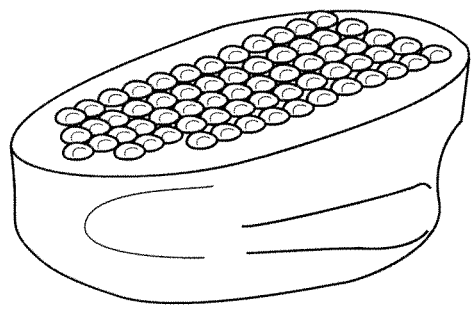
Figure 5A:
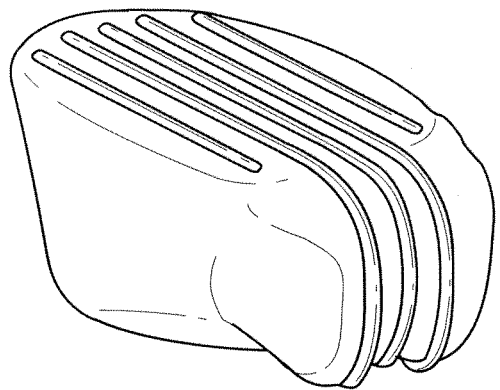
FIGS. 5A-B show an embodiment of the applicator of the skin rejuvenation device.
Figure 5B:
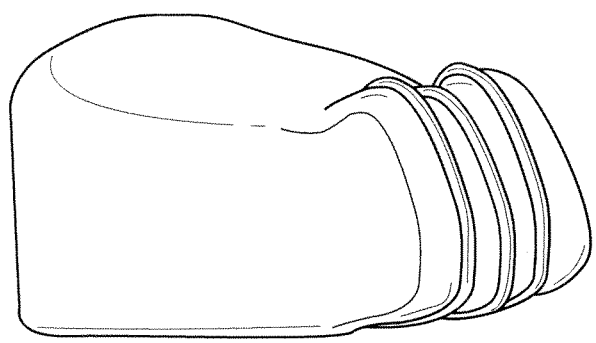
Figure 6A:
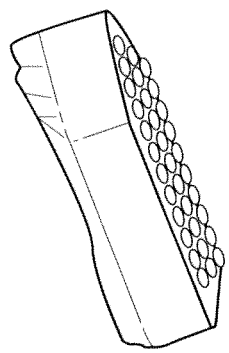
FIGS. 6A-C show an embodiment of the applicator of the skin rejuvenation device.
Figure 6B:
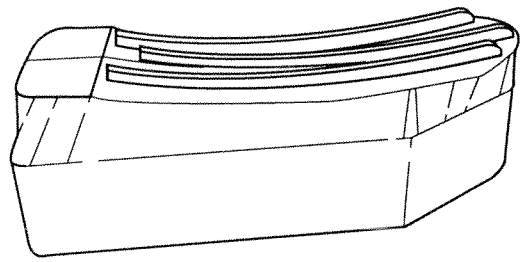
Figure 6C:
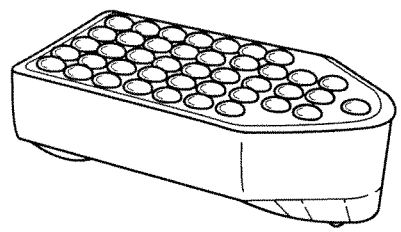
Figure 7A:
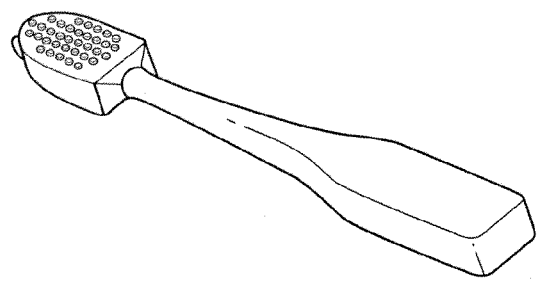
FIGS. 7A-D show an embodiment of the applicator of the skin rejuvenation device.
Figure 7B:
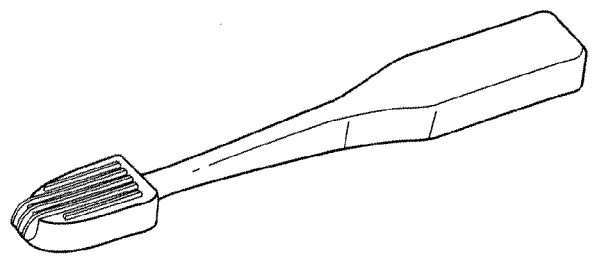
Figure 7C:
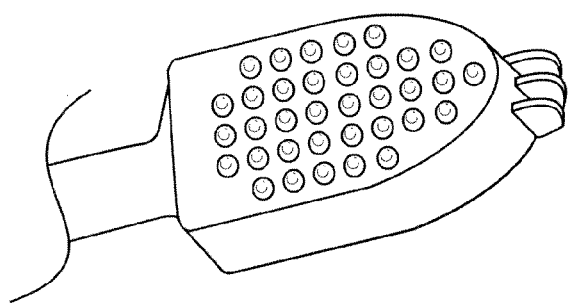
Figure 7D:
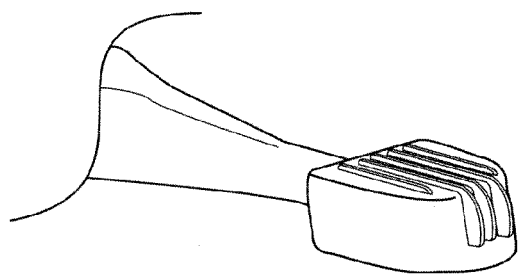
Figure 8A:
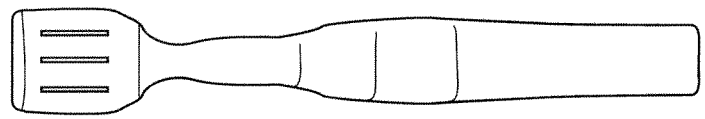
FIGS. 8A-C show an embodiment of the applicator of the skin rejuvenation device.
Figure 8B:
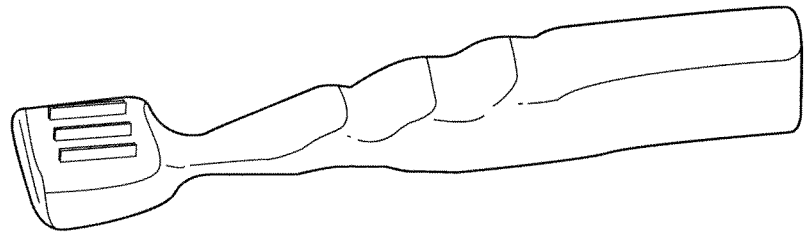
Figure 8C:
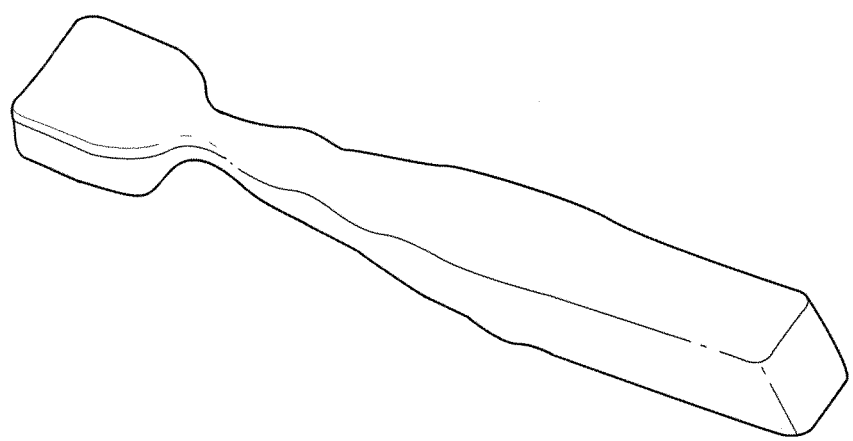

In a particular embodiment, the cable or multiple cables connecting the applicator to the remainder of the components comprise multiple wires as depicted in FIG. 3. The multiple wires are capable of simultaneously transmitting signals of different intensity, amplitude, or frequency to the electrodes, transducers or light sources. In particular embodiments, the multiple wires comprise at least 3 wires, having at least one common wire, at least one wire for controlling at least one electrode and at least one wire for controlling at least one light source. In other particular embodiments, the multiple wires comprise at least 3 wires, having at least one common wire, at least one wire for controlling at least one transducer and at least one wire for controlling at least one light source. In other particular embodiments, the multiple wires comprise at least 3 wires, having at least one common wire, at least one wire for controlling at least one electrode and at least one wire for controlling at least one transducer. In different particular embodiments, the multiple wires comprise at least 4 wires, having at least one common wire, at least one wire for controlling at least one electrode, at least one wire for controlling at least one transducer and at least one wire for controlling at least one transducer.

Applicator

In a particular embodiment, the applicator is hand-held. In a further embodiment, the hand-held applicator is mouse-shaped, as exemplified in FIGS. 2A-D, 4A-C, 5A-B and 6A-C. In a further embodiment, the hand-held applicator is wand-shaped, as exemplified in FIGS. 7A-D and 8A-C. In another embodiment, the applicator is a mask. In another embodiment, the applicator is contoured to conform to the shape of a particular region of the face, head or another part of the body. In another embodiment, the applicator is flexible.

The applicator component comprises an array of electrodes comprising a conductive material, light sources and/or transducers that can be moved over the biological tissue and provide energy stimulation to the skin. In a particular embodiment, the array comprises one or more positive electrodes and one or more negative electrodes. In some embodiments, the conductive material may be a metal. In particular embodiments, the metal may be stainless steel, aluminum, gold, silver, titanium, copper, zinc, magnesium or any other suitable metal or metal alloy.

In a further embodiment, the array comprises at least two positive electrodes. In a further embodiment, the array comprises at least three positive electrodes. In a further embodiment, the array comprises at least four positive electrodes. In a further embodiment, the array comprises at least five positive electrodes. In a further embodiment, the array comprises at least 10, 15, 20, 25 or 50 positive electrodes.

In another further embodiment, the array comprises at least two negative electrodes. In a further embodiment, the array comprises at least three negative electrodes. In a further embodiment, the array comprises at least four negative electrodes. In a further embodiment, the array comprises at least five negative electrodes. In a further embodiment, the array comprises at least 10, 15, 20, 25 or 50 negative electrodes.

In another embodiment, the number of positive electrodes is the same as the number of negative electrodes. In a further embodiment, the number of positive electrodes is greater than the number of negative electrodes. In a different further embodiment, the number of negative electrodes is greater than the number of positive electrodes.

In one aspect of the present device, the electrodes are individual pins as exemplified in FIGS. 4B, 4C, 6A, 6C, 7A, and 7C. In particular embodiments, the pins may comprise a convex, rounded, flattened or pointed surface for contacting a biological tissue, such as skin. The surface of the pins may be flush with the surface of the applicator, or may protrude from the surface of the applicator. In some embodiments, the pins are polished. In some embodiments, individual pins are 1 mm or less in diameter. In some embodiments, individual pins are 1 mm or more in diameter. Also, in some embodiments, individual pins are about 1, 2, 3, 4, 5, 6, 7, 8, 9 or 10 mm in diameter. In some embodiments, individual pins may be of the same or different diameter. In particular embodiments, positive electrodes may be a larger diameter pin than negative electrodes. In other particular embodiments, negative electrodes may be a larger diameter pin than positive electrodes.

Figure 9A:
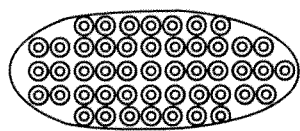
FIGS. 9A-C show an exemplary configuration for the arrangement of light sources, pin shaped electrodes or transducers.
Figure 9B:
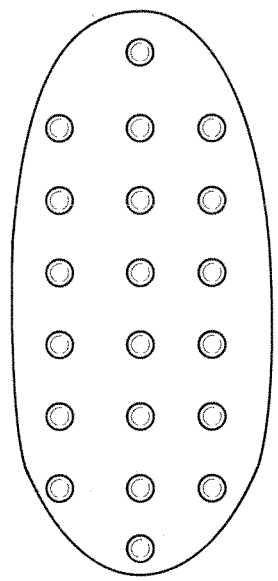
Figure 9C:
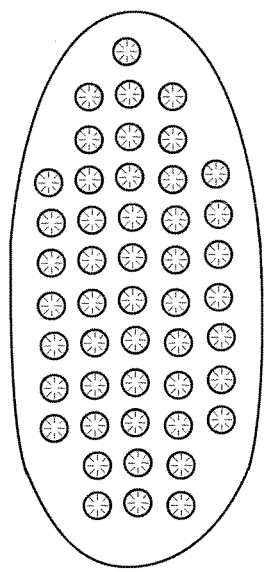

In a particular embodiment, the pins are arranged in rows, as illustrated in FIGS. 9A-C. In another embodiment, the pins are arranged in arcs, semi-circles, circles, waves or randomly.

In particular embodiments, individual pins may be at least 1 mm apart from one another on the surface of the applicator. In other particular embodiments, individual pins may be at least 2, 3, 4, 5, 6, 7, 8, 9, 10, 15 or 20 mm apart from one another on the surface of the applicator.

In another aspect of the present device, the electrodes are blade shaped, as exemplified in FIGS. 5A, 5B, 6A, 6B, 7B, 7D, 8A and 8B. In related embodiments, the blade shaped electrodes may be parallel to one another or may be at acute, right, or obtuse angles to one another. In particular embodiments, the blade shaped electrodes may comprise a convex, rounded, flattened or pointed surface for contacting a biological tissue, such as skin. The surface of the blade shaped electrodes may be flush with the surface of the applicator, or may protrude from the surface of the applicator. In some embodiments, the blade shaped electrodes are polished.

In some embodiments, individual blade shaped electrodes are 1 mm or less in width. In some embodiments, individual blade shaped electrodes are about 1 mm or more in width. Also, in some embodiments, individual blade shaped electrodes are about 1, 2, 3, 4, 5, 6, 7, 8, 9 or 10 mm in width. In some embodiments, individual blade shaped electrodes may be of the same or different width. In particular embodiments, positive electrodes may be a greater width than negative electrodes. In other particular embodiments, negative electrodes may be a greater width than positive electrodes.

In particular embodiments, individual blade shaped electrodes may be at least about 1 mm apart from one another on the surface of the applicator. In other particular embodiments, individual blade shaped electrodes may be at least 2, 3, 4, 5, 6, 7, 8, 9, 10, 15 or 20 mm apart from one another on the surface of the applicator.

In particular embodiments, the applicator comprises both pin shaped and blade shaped electrodes. In a further embodiment, the pin shaped and blade shaped electrodes are on the same face of the applicator. In another embodiment, the pin shaped and blade shaped electrodes are on different faces of the applicator as exemplified in FIGS. 6A, 7C and 7D.

In a particular embodiment, the skin rejuvenation device of the present application is capable of delivering a microcurrent in the attoampere range to the milliampere range. In a further embodiment, the device is capable of delivering a microcurrent in the attoampere range to the microampere range. In a further embodiment, the device is capable of delivering a microcurrent in the attoampere range to the nanoampere range. In a further embodiment, the device is capable of delivering a microcurrent in the attoampere range to the picoampere range. In a further embodiment, the device is capable of delivering a microcurrent in the attoampere range to the femtoampere range. In a further embodiment, the device is capable of delivering a microcurrent in the femtoampere range to the microampere range. In a further embodiment, the device is capable of delivering a microcurrent in the picoampere range to the microampere range. In a further embodiment, the device is capable of delivering a microcurrent in the nanoampere range to the microampere range. In another further embodiment, the device is capable of delivering a microcurrent in the attoampere range. In another further embodiment, the device is capable of delivering a microcurrent in the femtoampere range. In another further embodiment, the device is capable of delivering a microcurrent in the picoampere range. In another further embodiment, the device is capable of delivering a microcurrent in the nanoampere range. In another further embodiment, the device is capable of delivering a microcurrent in the microampere range. In another further embodiment, the device is capable of delivering a microcurrent that mimics or is similar in magnitude to the natural electrical communications known to regulate cellular activities.

In another particular embodiment, the microcurrent delivered by the skin rejuvenation device is between about one attoampere and about five milliamperes. In a further embodiment, the microcurrent is between about one attoampere and about four milliamperes. In a further embodiment, the microcurrent is between about one attoampere and about three peres. In a further embodiment, the microcurrent is between about one attoampere and about two milliamperes. In a further embodiment, the microcurrent is between about one attoampere and about one milliampere. In a further embodiment, the microcurrent is between about one attoampere and about one microampere. In a further embodiment, the microcurrent is between about one attoampere and about one nanoampere. In a further embodiment, the microcurrent is between about one attoampere and about one picoampere. In a further embodiment, the microcurrent is between about one attoampere and about one femtoampere.

In another embodiment, the microcurrent delivered by the skin rejuvenation device is less than about 1, 0.9, 0.8, 0.7, 0.6, 0.5, 0.4, 0.3, 0.2 or 0.1 milliampere. In another further embodiment, the microcurrent is less than about 0.09, 0.06, 0.03, or 0.01 milliamperes. In another further embodiment, the microcurrent is less than about 0.009, 0.006, 0.003, or 0.001 milliamperes.

Another aspect of the present application is a skin rejuvenation device for stimulating skin cells and underlying tissues with photonic stimulation for causing predetermined physiological changes in said skin cells and underlying tissues.

In particular embodiments, the applicator comprises one or more light sources for delivering photonic energy to the skin and underlying tissue. The light source can be any suitable type of light source, however, in a preferred embodiment the light source is a light-emitting diode (LED). In a further embodiment, the applicator comprises an array of light sources, having at least two light sources. In a further embodiment, the array comprises at least three light sources. In a further embodiment, the array comprises at least four light sources. In a further embodiment, the array comprises at least five light sources. In a further embodiment, the array comprises at least 10, 15, 20, 25 or 50 light sources.

In particular embodiments, individual light sources may be at least 1 mm apart from one another on the surface of the applicator. In other particular embodiments, individual light sources may be at least 2, 3, 4, 5, 6, 7, 8, 9, 10, 15 or 20 mm apart from one another on the surface of the applicator.

In particular embodiments, the photonic energy transmitted by a light source of the skin rejuvenation device is white light. In one embodiment, the photonic energy is in the infrared region of the spectrum. In another embodiment, the photonic energy is in the near-infrared region of the spectrum. In another embodiment, the photonic energy is in the red region of the spectrum. In another embodiment, the photonic energy is in the orange region of the spectrum. In another embodiment, the photonic energy is in the yellow region of the spectrum. In another embodiment, the photonic energy is in the green region of the spectrum. In another embodiment, the photonic energy is in the blue region of the spectrum. In another embodiment, the photonic energy is in the violet region of the spectrum. In another embodiment, the photonic energy is in the ultraviolet region of the spectrum. In some embodiments, each of the light sources on the applicator transmits photonic energy from the same region of the spectrum. In some embodiments, individual light sources on the applicator transmit photonic energy from different regions of the spectrum. As a non-limiting example, some of the light sources on the applicator transmit photonic energy as white light, while other light sources on the applicator transmit photonic energy in the infrared region. In another embodiment, at least one light source on the applicator is capable of transmitting photonic energy in more than one region of the spectrum, wherein the region of the spectrum in which it is being used is modulated using the intensity control.

Figure 10:
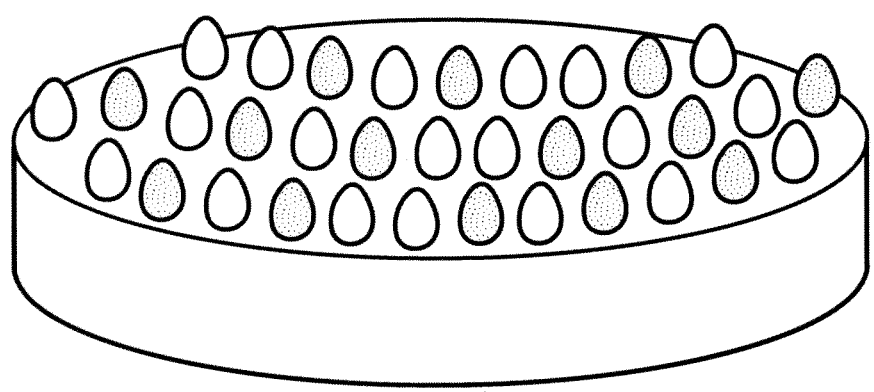
FIG. 10 shows an illustration of an exemplary arrangement of light sources with pin shaped electrodes or transducers on a face of an applicator of the skin rejuvenation device.

Another aspect of the present application is directed to a device for stimulating skin cells and underlying tissues with electrical microcurrents and photonic stimulation for causing predetermined physiological changes in said skin cells and underlying tissues. In still another aspect of the present device, the applicator component comprises one or more positive electrodes for delivering electrical energy, one or more negative electrodes, and one or more light sources for delivering photonic energy to the skin and underlying tissue, as shown in FIG. 10.

In a particular embodiment, the light sources are interspersed with the electrodes, which may be pin or blade shaped electrodes. In another embodiment, light sources are located between negative and positive electrodes. In another embodiment, at least one positive and at least one negative electrode are located between at least two light sources. In another embodiment, electrodes and light sources are located on different faces of the applicator.

Another aspect of the present application is a skin rejuvenation device for stimulating skin cells and underlying tissues with sonic or ultrasonic stimulation for causing predetermined physiological changes in said skin cells and underlying tissues.

In particular embodiments, the applicator comprises one or more transducers for delivering sonic or ultrasonic energy to the skin and underlying tissue. In a further embodiment, the applicator comprises an array of transducers, having at least two transducers. In a further embodiment, the array comprises at least three transducers. In a further embodiment, the array comprises at least four transducers. In a further embodiment, the array comprises at least five transducers. In a further embodiment, the array comprises at least 10, 15, 20, 25 or 50 transducers.

In one aspect of the present device, the transducers are individual pins. In particular embodiments, the pins may comprise a convex, rounded, flattened or pointed surface for contacting a biological tissue, such as skin. The surface of the pins may be flush with the surface of the applicator, or may protrude from the surface of the applicator. In some embodiments, the pins are polished. In some embodiments, individual pins are 1 mm or less in diameter. In some embodiments, individual pins are 1 mm or more in diameter. Also, in some embodiments, individual pins are about 1, 2, 3, 4, 5, 6, 7, 8, 9 or 10 mm in diameter. In some embodiments, individual pins may be of the same or different diameter.

In another aspect of the present device, the transducers are blade shaped. In related embodiments, the blade shaped transducers may be parallel to one another or may be at acute, right, or obtuse angles to one another. In particular embodiments, the blade shaped transducers may comprise a convex, rounded, flattened or pointed surface for contacting a biological tissue, such as skin. The surface of the blade shaped transducers may be flush with the surface of the applicator, or may protrude from the surface of the applicator. In some embodiments, the blade shaped transducers are polished.

In particular embodiments, individual transducers may be at least 1 mm apart from one another on the surface of the applicator. In other particular embodiments, individual transducers may be at least 2, 3, 4, 5, 6, 7, 8, 9, 10, 15 or 20 mm apart from one another on the surface of the applicator.

Another aspect of the present application is directed to a device for stimulating skin cells and underlying tissues with electrical microcurrents and sonic or ultrasonic stimulation for causing predetermined physiological changes in said skin cells and underlying tissues. In still another aspect of the present device, the applicator component comprises one or more positive electrodes for delivering electrical energy, one or more negative electrodes, and one or more transducers for delivering sonic or ultrasonic energy to the skin and underlying tissue.

In a particular embodiment, the transducers are interspersed with the electrodes, which may be pin or blade shaped electrodes. In another embodiment, transducers are located between negative and positive electrodes. In another embodiment, at least one positive and at least one negative electrode are located between at least two transducers. In another embodiment, electrodes and transducers are located on different faces of the applicator.

Still another aspect of the present application is directed to a device for stimulating skin cells and underlying tissues with photonic stimulation and sonic or ultrasonic stimulation for causing predetermined physiological changes in said skin cells and underlying tissues. In still another aspect of the present device, the applicator component comprises one or more light sources for delivering photonic energy, and one or more transducers for delivering ultrasonic energy to the skin and underlying tissue. In a particular embodiment, the transducers, which may be pin or blade shaped, are interspersed with the light sources. In another embodiment, transducers and light sources are located on different faces of the applicator.

Yet another aspect of the present application is directed to a device for stimulating skin cells and underlying tissues with electrical microcurrents, photonic stimulation and sonic or ultrasonic stimulation for causing predetermined physiological changes in said skin cells and underlying tissues. In still another aspect of the present device, the applicator component comprises one or more positive electrodes for delivering electrical energy, one or more negative electrodes, one or more light sources for delivering photonic energy, and one or more transducers for delivering sonic or ultrasonic energy to the skin and underlying tissue. In a particular embodiment, the transducers are located on the same face of the applicator with the light sources and the electrodes. In another particular embodiment, the transducers are located on the same face of the applicator with the light sources, while the electrodes are located on a different face of the applicator. In another particular embodiment, the transducers are located on the same face of the applicator with the electrodes, while the light sources are located on a different face of the applicator. In another particular embodiment, the electrodes are located on the same face of the applicator with the light sources, while the transducers are located on a different face of the applicator. In another particular embodiment, the electrodes, light sources, and transducers are located on different faces of the applicator.

In a particular embodiment, the skin rejuvenation device of the present application is used without the presence of additional chemicals or other substances on the skin. In other embodiments, the skin rejuvenation device can be used in conjunction with the application of additional chemicals or substances for skin treatment or lubrication. Said additional chemicals or substances for skin treatment or lubrication include, but are not limited to, water (including, but not limited to, filtered, demineralized, spring or distilled water), organic oils (including, but not limited to, aloe vera oil, olive oil, mineral oil), Botulinum Toxin Type A (or other paralytic agents), collagen, dermal fillers, epidermal growth factor, vitamin A, aloe, retin-A, gelatin, chemical peels, lotions, cream, food products, and plant extracts.

Intensity Control and Signal Creation Source

The intensity control of the skin rejuvenation device modulates the energy signals from the signal creation source (signal replicator) to the electrodes, light sources and/or transducers, as depicted in FIG. 6. The intensity control can selectively modify the signal properties such as amplitude, pulse rate, pulse sweep, frequency, frequency sweep rate, duty cycle and other parameters to provide different electrical, photonic, sonic, ultrasonic or other forms of direct or radiant stimulation to the tissue. The intensity control can also provide electronically for different patterns of activation of the various electrodes, photonic sources and/or transducers, thereby constructively altering the depth and area of stimulation by choosing which electrodes, photonic sources and/or transducers are active and thereby influencing the patterns or geometry of the stimulus delivery.

In a particular embodiment, the intensity control is capable of modulating more than one pattern of energy distribution from the signal creation source to the applicator at a time. In another particular embodiment, the intensity control is capable of modulating more than frequency to the applicator at a time.

Figure 11:
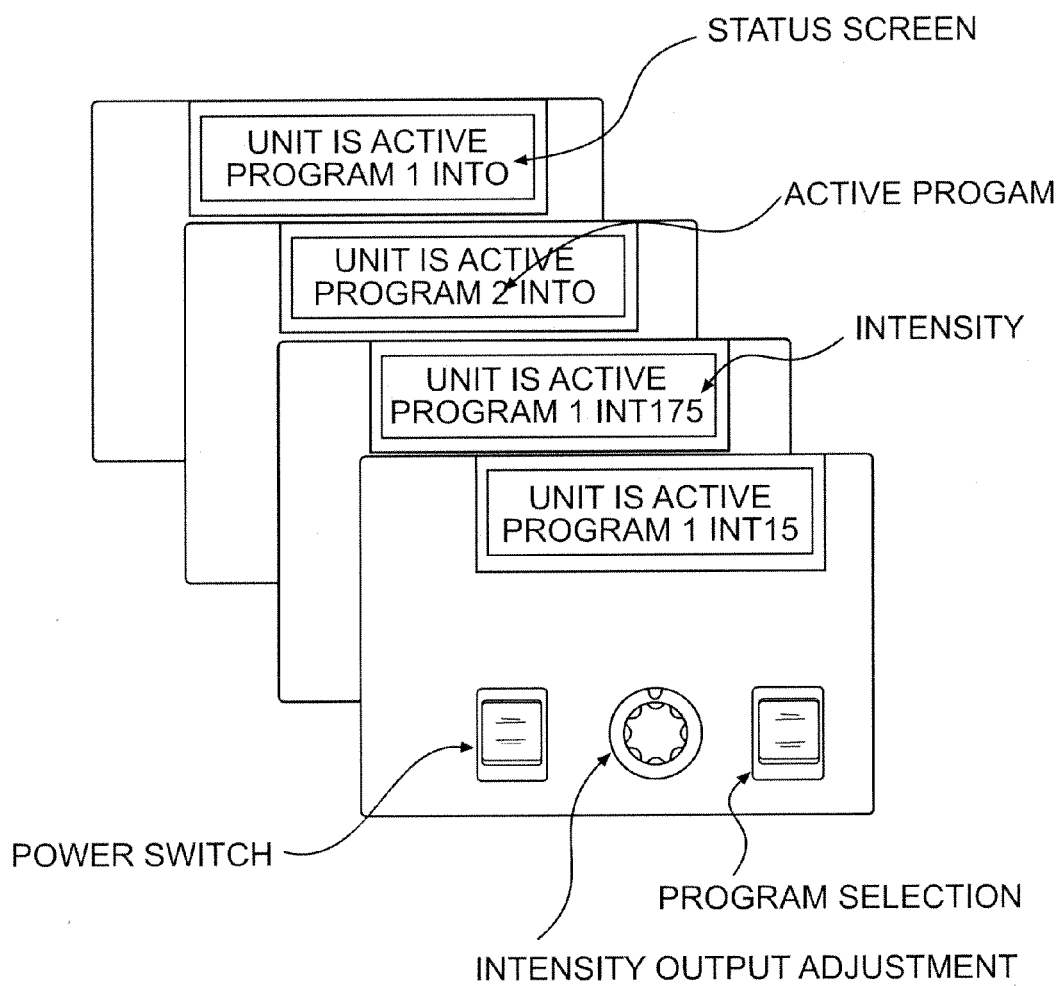
FIG. 11 depicts an exemplary intensity control and display of the skin rejuvenation device.

The intensity control provides means for independently controlling the energy supplied to the electrode, photonic and/or transducer arrays, thereby providing electrical, photonic, radiant, sonic or ultrasonic stimulation of skin in specific geometric patterns that can be selected for optimal effects on the skin of a person. In a particular embodiment, the energy is provided to the applicator as pulsating voltage. In another particular embodiment, the energy is provided to the applicator as steady voltage. In particular embodiments, the intensity control comprises a display as depicted in FIG. 11. The display allows the user to select between various signal characteristics and patterns of electrode, light source and/or transducer activity and provides controls for selectively modifying the output signal function.

Figure 12:
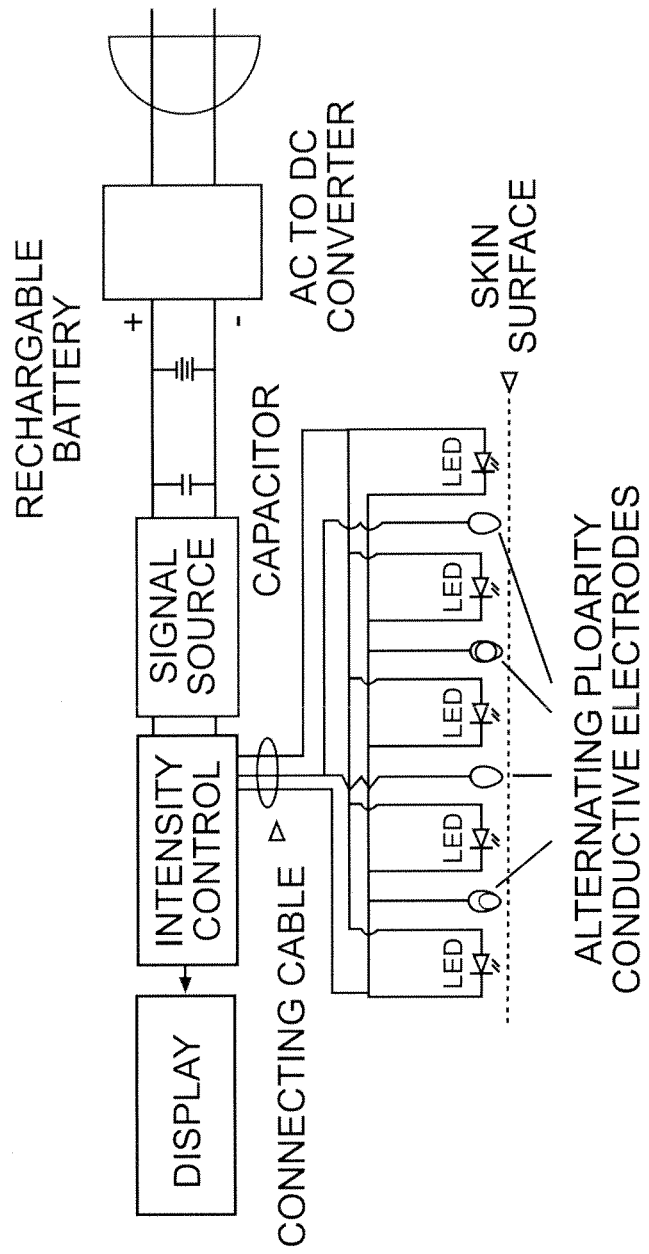
FIG. 12 shows an illustration of an examplery schematic of the circuitry of the skin rejuvenation device.

In a particular embodiment, each of the electrodes, light sources or transducers of the present skin rejuvenation device are independently powered through the intensity control as depicted in the exemplary schematic of FIG. 12. In another embodiment, the electrodes, light sources or transducers of the present skin rejuvenation device are powered through the intensity control in groups or clusters.

The signal creation source of the skin rejuvenation device is capable of producing a pure, low noise, square wave electrical signal with a wide range of currents and frequencies that can be selected for optimal effects on the skin of a person. Using frequencies with variable amplitudes allow for the digital emulation of analog signals.

In a particular embodiment, the frequency of the signal that is provided to the applicator is between about 1 kiloHertz (kHz) and about 100 kHz. In a further particular embodiment, the frequency of the signal that is provided to the applicator is between about 10 kHz and about 90 kHz. In a still further particular embodiment, the frequency of the signal that is provided to the applicator is between about 20 kHz and about 80 kHz. In a yet further particular embodiment, the frequency of the signal that is provided to the applicator is between about 30 kHz and about 70 kHz. In yet another particular embodiment, the frequency of the signal that is provided to the applicator is between about 40 kHz and about 70 kHz. In one particular embodiment, the frequency of the signal that is provided to the applicator is between about 40 kHz and about 50 kHz. In another particular embodiment, the frequency of the signal that is provided to the applicator is about 70 kHz.

Power Supply

The power supply of the skin rejuvenation device comprises a capacitor in parallel with the electrical source. In a particular embodiment, the capacitor is large or over-sized. The capacitor allows for a constant voltage supply to the oscillator circuit of the signal creation source regardless of the loads imposed by the oscillator as it is switched between different operating modes. Without the capacitor the power supply will not function as a constant voltage and current source because of surges or demands and parasitic resistive and capacitive loads produced by active components of the device. This would result in phase noise and other forms of distortion in the oscillator output. By using the large capacitor and a solid state, high speed switching device, such as a field-effect transistor, the present device is provided with the means to generate a robust low noise variable-frequency oscillator with the use of very few components.

In a particular embodiment, the size of the capacitor is between about 10 and about 500,000 microfarads. In a further particular embodiment, the size of the capacitor s between about 100 and about 100,000 microfarads. In another further particular embodiment, the size of the capacitor is between about 1,000 and about 50,000 microfarads. In still another further particular embodiment, the size of the capacitor is between about 5,000 and about 50,000 microfarads. In yet another further particular embodiment, the size of the capacitor is about 10,000 microfarads.

In particular embodiments, energy is supplied to the power supply by a battery. In a further embodiment, the battery is a rechargeable battery. In another embodiment, energy is supplied to the power supply by an external power source.

Method of Skin Rejuvenation

Another aspect of the present invention relates to a method for anti-aging comprising contacting the skin of the subject with a device of comprising contacting the skin of the subject to a device comprising an applicator comprising at least one positive electrode and at least one negative electrode for the stimulation of skin and underlying tissues with electric microcurrents, a intensity control for modulating the microcurrent delivery to the electrodes, and a signal creation source for providing electrical signals to the intensity control, wherein the device is capable of delivering a microcurrent in the attoampere range to the microampere range.

Another aspect of the present invention relates to a method for stimulating a skin cell or tissue comprising contacting said skin cell a device comprising: an applicator comprising at least one light source for the stimulation of said skin cell and underlying tissue with photonic stimulation, a intensity control for modulating the current delivery to the light source, and a signal creation source for providing electrical signals to the intensity control.

Another aspect of the present invention relates to a method for enhancing a skin cell growth comprising contacting said skin cell to a skin rejuvenation device comprising: an applicator comprising at least one positive electrode and at least one negative electrode for the stimulation of skin and underlying tissues with electric microcurrents and at least one light source for the stimulation of said skin cell and underlying tissues with photonic stimulation, a intensity control for modulating the microcurrent delivery to the electrodes and current delivery to the light source, and a signal creation source for providing electrical signals to the intensity control.

In a particular embodiment, the anti-aging method or the method of stimulating skin cells relates to reducing the appearance of wrinkles in the subject. In a further embodiment, the wrinkles include glabellar lines, nasolabial folds, fine lines, marionette lines, smile lines, or deep lines.

In another embodiment, the anti-aging method or the method of stimulating skin cells provides for use of a skin rejuvenation device of the present application on the skin of a subject having at least one condition selected from the group consisting of, sagging facial muscles, acne or other skin infections, rosacea, hyper-pigmentation, cellulite, hair growth regulation, sunburn, skin texture, skin firmness, skin elasticity, skin vasculature, dark circles, sebum regulation, impetigo, folliculitis, furunculosis, ecthyma, eczema, psoriasis, atopic dermatitis, herpes, epidermolysis bullosa, icthyosis, and traumatic lesions (e.g., scars, ulcers, minor burns, cuts, abrasions, lacerations, warts, blisters, birthmarks, moles, wounds, biopsy sites, surgical incisions and insect bites).

In a particular embodiment, parameters for the microcurrent and/or photonic stimulation of the device are set using the intensity control and the applicator is contacted with the area of skin and underlying tissue. In a particular embodiment, the applicator is contacted with the area of skin and underlying tissue before parameters for the microcurrent and/or photonic stimulation of the device are set using the intensity control. In another particular embodiment, the applicator is contacted with the area of skin and underlying tissue after parameters for the microcurrent and/or photonic stimulation of the device are set using the intensity control.

In a particular embodiment, the applicator of the skin rejuvenation device is held in a single location of the skin and underlying tissue. In another particular embodiment, the applicator of the skin rejuvenation device is moved in a linear manner over the skin and underlying tissue. In another particular embodiment, the applicator of the skin rejuvenation device is moved back and forth over the skin and underlying tissue. In another particular embodiment, the applicator of the skin rejuvenation device is moved in a circular manner over the skin and underlying tissue. In a further embodiment, the circular manner comprises movement in concentric circles from the center of movement and expanding outward. In another further embodiment, the circular manner comprises movement in concentric circles starting with a wide circle and contracting toward the center. In another further embodiment, the circular manner comprises movement in overlapping circles. In yet another particular embodiment, the applicator of the skin rejuvenation device is moved in a random manner over the skin and underlying tissue.

In a particular embodiment, the device is used for rejuvenating skin four times (or sessions) per day. In another embodiment, the device is used three times per day. In another embodiment, the device is used two times per day. In another embodiment, the device is used one time per day. In another embodiment, the device is used every other day. In another embodiment, the device is used every third day. In another embodiment, the device is used every fourth day. In another embodiment, the device is used every fifth day. In another embodiment, the device is used one day per week. In another embodiment, the device is used one day each two weeks. In another embodiment, the device is used one day per month.

In a particular embodiment, an individual session of using the device for rejuvenating skin is about 60 minutes or more. In another embodiment, a session is about 45 minutes. In another embodiment, a session is about 30 minutes. In another embodiment, a session is about 20 minutes. In another embodiment, a session is about 15 minutes. In another embodiment, a session is about 10 minutes. In another embodiment, a session is about 5 minutes or less. In another embodiment, a session is between about 5 minutes and about 60 minutes.

In particular embodiments, the skin rejuvenation device of the present application is used on the face. In further embodiments, the device is used on the forehead, eyelids, under the eyes, cheeks, nose, upper lip, chin or neck. In another embodiment, the device is used on the scalp. In another embodiment, the device is used on the back. In another embodiment, the device is used on the chest. In another embodiment, the device is used on the abdomen. In another embodiment, the device is used on the buttocks. In another embodiment, the device is used on the pelvic region. In another embodiment, the device is used on the upper arm. In another embodiment, the device is used on the lower arm. In another embodiment, the device is used on the back of the hand. In another embodiment, the device is used on the thigh or upper leg. In another embodiment, the device is used on the calf or lower leg. In another embodiment, the device is used on the foot. The artisan would readily understand that the use of the present device during a particular session can be on any of these areas of the body either alone or in any combination.

The present device is further illustrated by the following example which should not be construed as limiting. The contents of all references, patents and published patent applications cited throughout this application, as well as the Figures and Tables, are incorporated herein by reference.

EXAMPLE 1

Reduction of Facial Wrinkles in a Subject

In order to help the applicator glide smoothly on the skin, the skin is optionally moisturized for lubrication. Filtered water or organic oil is lightly applied to the skin.

The device is turned on and displays the current settings and/or the readiness of the device for use.

The operator of the device adjusts the intensity of the device to a desired setting, as displayed on the device, for use during a session.

In order to reduce the appearance of facial wrinkles on a subject, the device is slowly moved, in no particular order, over the forehead, eyelids, under the eyes, cheeks, nose, upper lip, chin and neck.

In order to achieve the desired reduction in facial wrinkles, the device is used for 30 minute sessions two times per day for about four to six weeks.

Following initial reduction of wrinkles the device is used one time per day for 15 minutes for maintenance of the rejuvenated skin condition.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. A device comprising:
   an applicator comprising at least one positive electrode and at least one negative electrode for the stimulation of skin and underlying tissues with electric currents,
   an intensity control that modulates frequency, and
   a signal creation source,
   wherein the device delivers a current in the attoampere range to the nanoampere range,
   wherein the frequency generated or delivered by the device is in the range of about 1,000Hz to about 350,000 Hz, and
   wherein the applicator comprises both pin shaped and blade shaped electrodes.

2. The device of claim 1, wherein the electrodes are pin shaped or blade shaped.

3. The device of claim 1, wherein the current is in the femtoampere range.

4. The device of claim 1, wherein the current is in the picoampere range.

5. The device of claim 1, wherein the current is in the nanoampere range.

6. The device of claim 1, wherein the intensity control further selectively modulates a signal property selected from the group consisting of amplitude, pulse rate, pulse sweep, frequency sweep rate, duty cycle and combinations thereof to provide different electrical currents to the skin and underlying tissues.

7. The device of claim 1, further comprising a power supply for supplying electrical current to the signal creation source.

8. The device of claim 7, wherein the power supply comprises a capacitor.

9. The device of claim 8, wherein the size of the capacitor is between about 1,000 and about 50,000 microfarads.

10. A method for anti-aging in a subject comprising contacting the skin of the subject to the device of claim 1.

11. A method for stimulating a skin cell or tissue in a subject comprising contacting the skin of the subject with a device comprising:
    an applicator comprising at least one positive electrode and at least one negative electrode for the stimulation of skin and underlying tissues with electric currents,
    an intensity control that modulates frequency, and
    a signal creation source,
    wherein the device delivers a current in the attoampere range to the nanoampere range,
    wherein the frequency generated or delivered by the device is in the range of about 1,000 Hz to about 350,000 Hz, and
    wherein the applicator comprises both pin shaped and blade shaped electrodes.

12. The device of claim 1, wherein the applicator comprises at least ten positive electrodes.

13. The device of claim 1, wherein the applicator comprises at least ten negative electrodes.

14. The device of claim 1, wherein the electrodes are arranged in rows.

* * * * *